(12) United States Patent
Zhang

(10) Patent No.: US 12,213,785 B2
(45) Date of Patent: Feb. 4, 2025

(54) LANCET

(71) Applicant: Tianjin Huahong Technology Co. Ltd., Tianjin (CN)

(72) Inventor: Libo Zhang, Tianjin (CN)

(73) Assignee: TIANJIN HUAHONG TECHNOLOGY CO. LTD., Tianjin (CN)

(*) Notice: Subject to any disclaimer, the term of this patent is extended or adjusted under 35 U.S.C. 154(b) by 896 days.

(21) Appl. No.: 15/779,784

(22) PCT Filed: May 12, 2017

(86) PCT No.: PCT/CN2017/084085
§ 371 (c)(1),
(2) Date: May 29, 2018

(87) PCT Pub. No.: WO2018/126575
PCT Pub. Date: Jul. 12, 2018

(65) Prior Publication Data
US 2021/0169385 A1 Jun. 10, 2021

(30) Foreign Application Priority Data
Jan. 6, 2017 (CN) .......................... 201710010881.9

(51) Int. Cl.
*A61B 5/151* (2006.01)
*A61B 5/15* (2006.01)

(52) U.S. Cl.
CPC .... *A61B 5/15113* (2013.01); *A61B 5/150541* (2013.01); *A61B 5/150572* (2013.01);
(Continued)

(58) Field of Classification Search
CPC .......... A61B 5/15113; A61B 5/150541; A61B 5/150572; A61B 5/15117; A61B 5/1513;
(Continued)

(56) References Cited

U.S. PATENT DOCUMENTS

| | | | |
|---|---|---|---|
| 10,589,036 B2* | 3/2020 | Sanders | A61M 25/0625 |
| 2009/0036915 A1* | 2/2009 | Karbowniczek | A61B 5/150022 606/182 |

(Continued)

FOREIGN PATENT DOCUMENTS

| | | |
|---|---|---|
| CN | 101959459 A | 1/2011 |
| CN | 101987016 A | 3/2011 |

(Continued)

*Primary Examiner* — Benjamin S Melhus
*Assistant Examiner* — Severo Antonio P Lopez
(74) *Attorney, Agent, or Firm* — Scully, Scott, Murphy & Presser, P.C.

(57) ABSTRACT

Provided is a lancet which comprises: a housing provided with an inner sleeve guiding portion and a first needle core guiding portion; an inner sleeve provided inside the housing, wherein the front end of the inner sleeve has an inner sleeve needle outlet, and the inner sleeve is provided with a second needle core guiding portion; a needle core adapted to move axially along the first needle core guiding portion; a spring provided inside the housing to drive the needle core, wherein the inner sleeve guiding portion has a radial rotation angle at a rotation guiding section thereof away from the inner sleeve needle outlet; by pressing towards the inside of the housing, the inner sleeve is guided by the rotation guiding section to rotate such that the first needle core guiding portion is aligned with the second needle core guiding portion in the radial direction.

11 Claims, 8 Drawing Sheets

(52) U.S. Cl.
CPC ........ *A61B 5/15117* (2013.01); *A61B 5/1513* (2013.01); *A61B 5/15144* (2013.01)

(58) Field of Classification Search
CPC ... A61B 5/1514; A61B 5/151; A61B 5/15101; A61B 5/15107; A61B 5/15109; A61B 5/15111; A61B 5/15126; A61B 5/15128; A61B 5/15144; A61B 5/1519; A61B 5/15192
USPC ........................................................ 600/583
See application file for complete search history.

(56) References Cited

U.S. PATENT DOCUMENTS

2011/0288491 A1* 11/2011 Newman ............... A61M 5/326
604/198
2011/0313439 A1* 12/2011 Ishikura ............. A61B 5/15142
606/182

FOREIGN PATENT DOCUMENTS

| | | |
|---|---|---|
| CN | 102028479 A | 4/2011 |
| CN | 201939346 U | 8/2011 |
| JP | 2012120555 A | 6/2012 |

* cited by examiner

LANCET

TECHNICAL FIELD

The present disclosure relates to the field of medical devices, more particularly, to a lancet.

BACKGROUND

For a lancet in the prior art, generally, a needle core is rotated to an emission position by pressing an inner sleeve, in this case, the inner sleeve is set to only slide axially within the housing of the lancet, while the needle core is set to rotate along an axis and move axially. However, because one end of a spring is connected with the needle core and the other end thereof is connected fixedly with a bottom cap of the lancet, the rotation of the needle core will cause the spring to twist, and the twisting in the course of tension of the spring results in loss of potential energy of the spring, which reduces elastic force applied to the needle core.

Besides, false emission should be avoided for the lancet. In the prior art, to prevent false emission, a cap is provided to the lancet to cover the inner sleeve which triggers the blood taking operation. However, the providing of the cap not only increases the number of components but also increases the manufacturing cost.

SUMMARY

The object of the present disclosure is to relieve or solve at least one of the above problems.

According to one aspect of the embodiment of the present disclosure, the present disclosure provides a lancet including:
- a housing provided with an inner sleeve guiding portion for guiding movement of an inner sleeve and a first needle core guiding portion for guiding movement of a needle core;
- the inner sleeve provided inside the housing and adapted to move along the inner sleeve guiding portion, wherein the front end of the inner sleeve has an inner sleeve needle outlet and the inner sleeve is provided with a second needle core guiding portion to guide the movement of the needle core;
- the needle core, the body of which is adapted to move axially along the first needle core guiding portion, and which is provided with a needle body;
- a spring provided inside the housing to drive the needle core to move axially towards the inner sleeve needle outlet, wherein
the inner sleeve guiding portion has a radial rotation angle at a rotation guiding section thereof away from the inner sleeve needle outlet;
by pressing towards the inside of the housing, the inner sleeve is guided by the rotation guiding section to rotate such that the first needle core guiding portion is aligned with the second needle core guiding portion in the radial direction.

Alternatively, the end of the rotary guiding section has a limiting end face perpendicular to the axial direction.

Alternatively, the radial rotation angle of the rotary guiding section is between 25° and 35°. Further, the inner sleeve is axially displaced by 2.5 mm-3.5 mm based on the guidance of the entire rotary guiding section.

Alternatively, a rear end of the inner sleeve adjacent to the second needle core guiding portion is provided with an abutment end face perpendicular to the axial direction, the needle core body is adapted to abut against the abutment end face, and the rotational movement of the inner sleeve causes the needle core body to be out of contact with the abutment end face and to move axially along the second needle core guiding portion.

Alternatively, the rear end of the inner sleeve is provided with a guiding unit which cooperates with the inner sleeve guiding portion.

In a further embodiment, the guiding unit is a guiding protrusion, and the guiding portions are guiding grooves.

Alternatively the inner sleeve guiding portion is provided inside with an inner sleeve positioning member which cooperates with the guiding unit to allow the guiding unit to pass over the inner sleeve positioning member in a direction of moving towards the rotary guiding section and to prevent the guide unit from passing through the inner sleeve positioning member in a direction of moving away from the rotary guiding section.

Alternatively, the guiding unit has a first guiding ramped surface and a first vertical blocking surface, wherein when the guiding unit moves towards the rotation guiding section, the first guiding ramped surface is adapted to be in contact with the inner sleeve positioning member, and after the guide unit passes over the inner sleeve positioning member, the first vertical blocking surface constitutes a blocking section that prevents the guiding unit from passing over the inner sleeve positioning member.

Alternatively, the inner sleeve positioning member has a second guiding ramped surface and a second vertical blocking surface, wherein the second guiding ramped surface cooperates with the first guiding ramped surface, and the second vertical blocking surface cooperates with the first vertical blocking surface.

Alternatively, the needle further includes a needle cap provided to the needle core body, wherein the needle cap passes through the inner sleeve through the inner sleeve needle outlet, the needle cap has a needle cap stopping member which abuts against an inner end face of the inner sleeve with the potential energy of the spring: the inner sleeve needle outlet is provided with an opening channel that allows the needle cap stopping member to pass through only in a specific orientation; the rear end of the inner sleeve is provided adjacent to the second needle core guiding portion with an abutment end face which is perpendicular to the axial direction, and the needle core body is adapted to abut against the abutment end face: in the case where the guiding unit passes over the inner sleeve positioning member and abuts against the inner sleeve positioning member, the distance between the needle core body and the abutment end face is in the range of 1 mm to 2 mm.

DETAILED DESCRIPTION OF PREFERRED EMBODIMENTS

Figure 1:
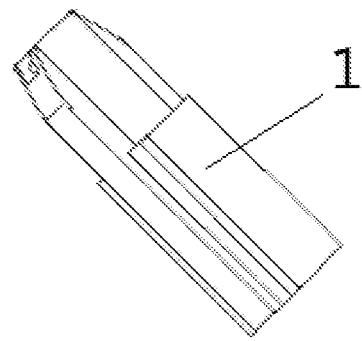
FIG. 1 is a schematic structural drawing of a housing of a lancet according to one exemplary embodiment of the present disclosure.

The technical solutions of the present disclosure will be described in detail below through embodiments in combination with the accompanied drawings. Throughout the specification, like reference numerals refer to like elements. The following description of the embodiments of the present disclosure with reference to the drawings is intended to explain the general inventive concept of the present disclosure and should not be understood as a limitation of the present disclosure.

Figure 2:
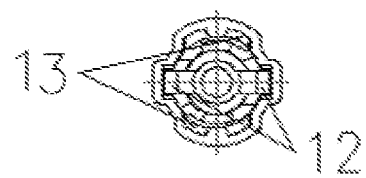
FIG. 2 is end view of the housing shown in FIG. 1.
Figure 3:
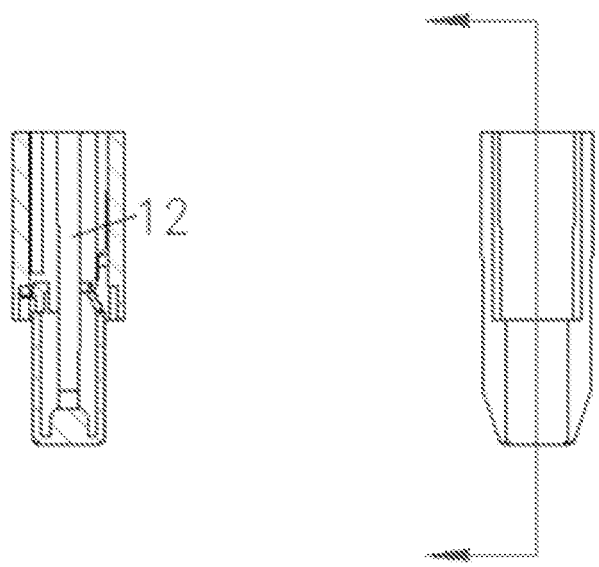
FIG. 3 is a schematic cross-sectional view of the housing shown in FIG. 1, and the position of the cross-section is illustrated on the right side.
Figure 4:
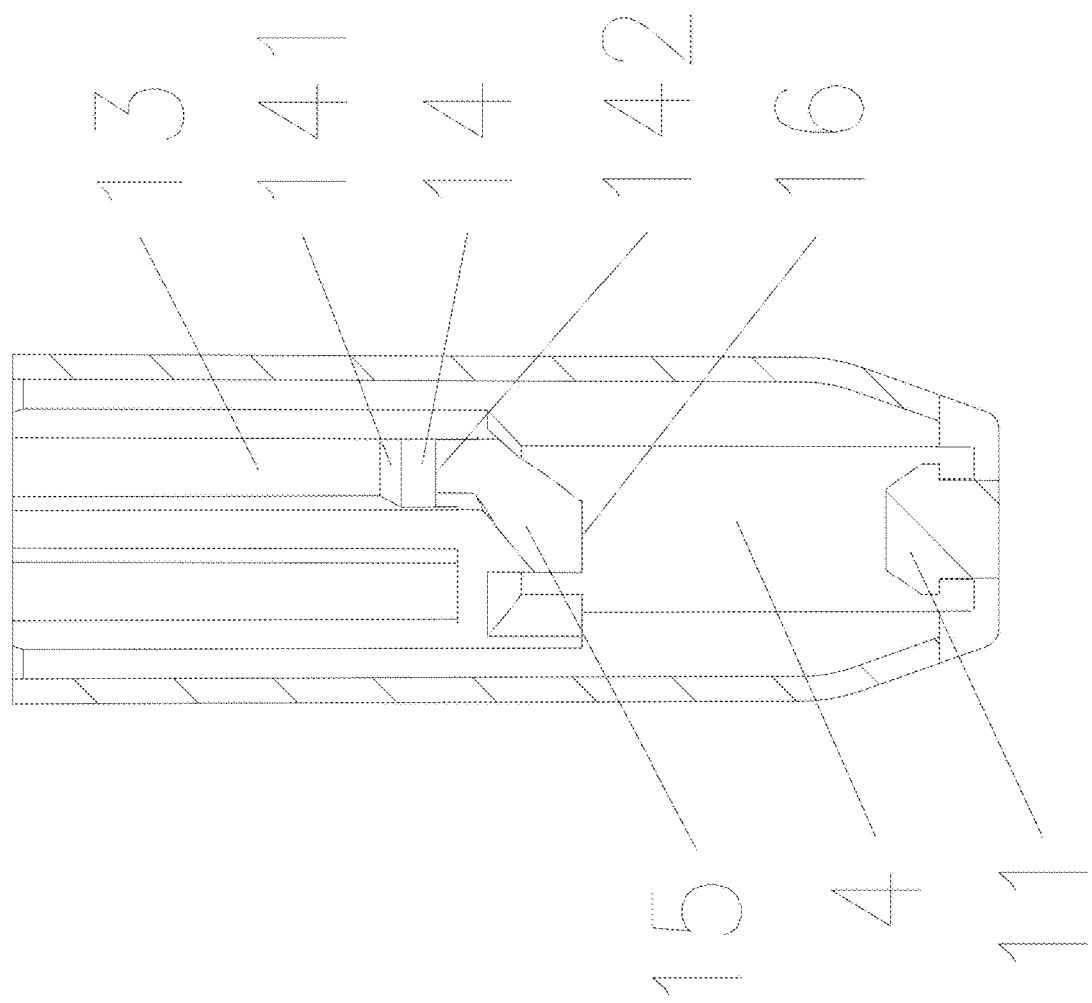
FIG. 4 is a schematic cross-sectional view of the housing shown in FIG. 1, and the position of the cross-section is illustrated on the left side.
Figure 4:
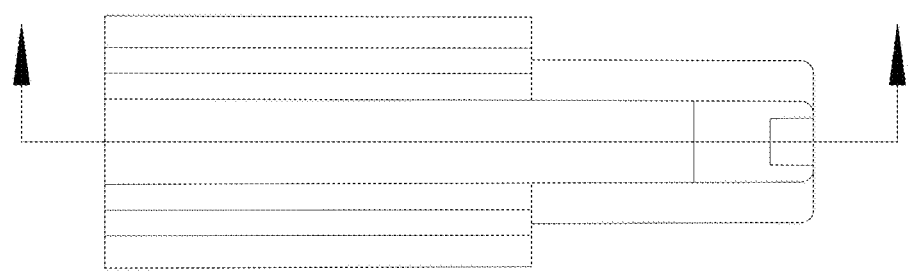
Figure 6:
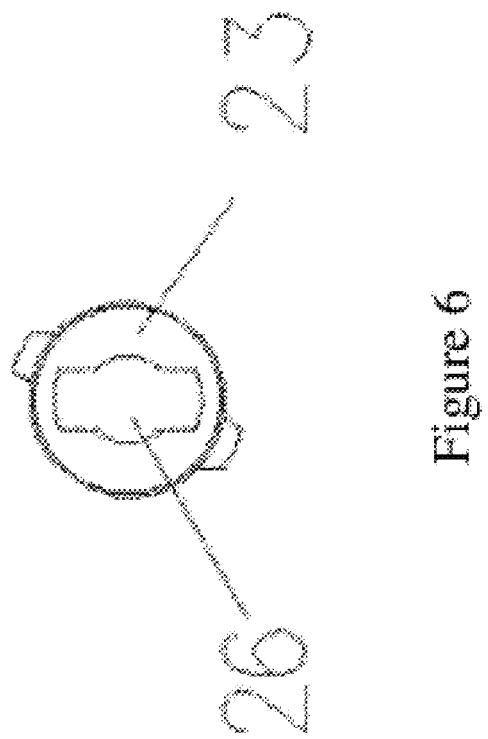
FIG. 6 is an end view of the inner sleeve shown in FIG. 5.
Figure 5:
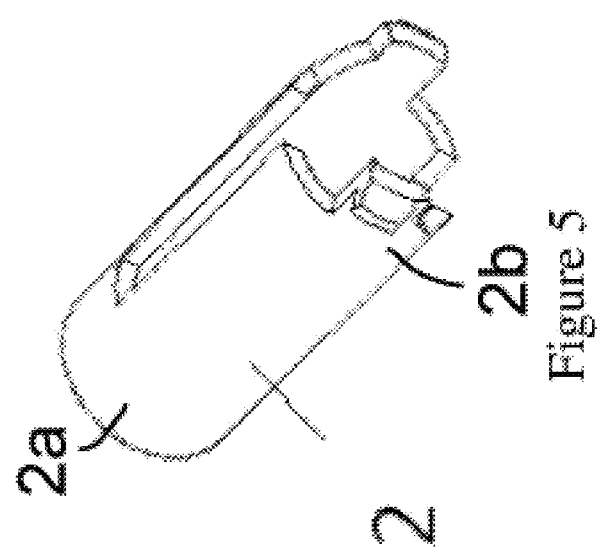
FIG. 5 is a schematic structural drawing of the inner sleeve of a lancet according to one exemplary embodiment of the present disclosure.
Figure 8:
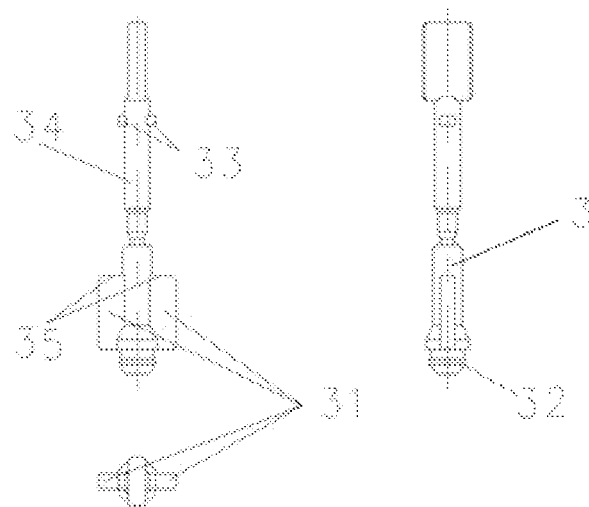
FIG. 8 is a schematic structural drawing of a needle core of a lancet according to one exemplary embodiment of the present disclosure.
Figure 9:
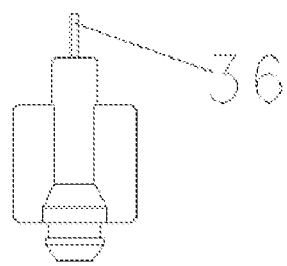
FIG. 9 is a schematic view of the needle core with the needle cap shown in FIG. 8 being removed.
Figure 10:
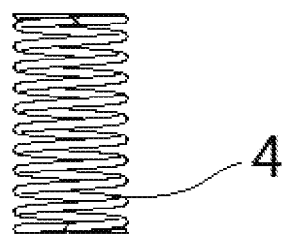
FIG. 10 is a schematic structural view of a spring of the lancet according to one exemplary embodiment of the present disclosure.
Figure 17:
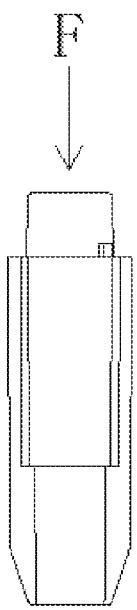
FIG. 17 is an operation schematic drawing of the lancet shown in FIG. 11 which is ready to be used.

First, refer to FIGS. 1 to 18, a lancet according to one exemplary embodiment of the present disclosure will be described in detail. It should be noted that, for the sake of clarity, some features or elements in the figures are not specifically illustrated. As shown in the figures, the lancet according to the present disclosure comprises:

a housing 1, as shown in FIG. 1, which is provided with an inner sleeve guiding portion 13 for guiding movement of an inner sleeve 2 and a first needle core guiding portion 12 for guiding the movement of a needle core 3, as shown in FIG. 2 and FIG. 3;

the inner sleeve 2, as shown in FIG. 5, which is provided inside the housing 1 and is adapted to move along the inner sleeve guiding portion 13, and as shown in FIG. 6, the front end 2a of the inner sleeve has an inner sleeve needle outlet 26, and the inner sleeve 2 is provided with a second needle core guiding portion 24 to guide the movement of the needle core;

the needle core 3, as shown in FIG. 8, the body of which is adapted to move axially along the first needle core guiding portion 12, and which is provided with a needle core body 36, as shown in FIG. 9;

a spring 4, as shown in FIG. 10, which is provided inside the housing 1 to drive the needle core 3 to move axially towards the inner sleeve needle outlet 26, wherein the axial direction is the axis direction of the housing.

wherein as shown in FIG. 4, the inner sleeve guiding portion 13 has a radial rotation angle at a rotation guiding section 15 thereof away from the inner sleeve needle outlet 26; by pressing towards the inside of the housing, for instance, by applying a force F as shown in FIG. 17, the inner sleeve 2 is guided by the rotary guiding section 15 to rotate such that the first needle core guiding portion 12 aligns with the second needle core guiding portion 24 in the radial direction.

Based on the above, the present disclosure provides a solution in which axial emission of the needle core 3 is achieved by rotational movement of the inner sleeve 2. Because the spring 4 is not twisted during pressing of the inner sleeve 2, the potential energy of the spring 4 is not reduced due to the twisting.

As shown in FIG. 4, the end of the rotary guiding section 15 has a limiting end face 16 perpendicular to the axial direction.

Figure 7:
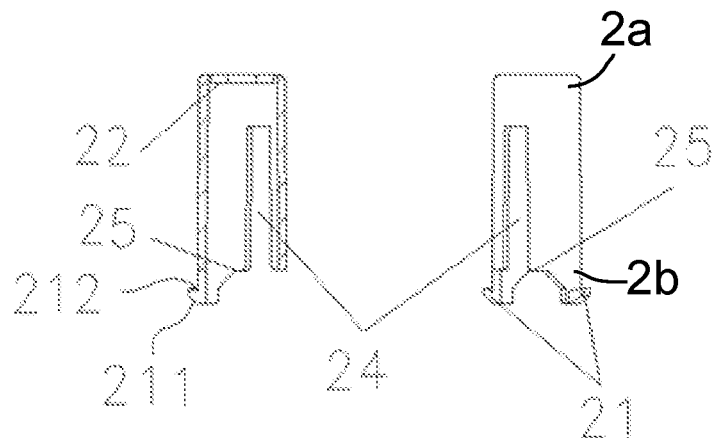
FIG. 7 is a view of the inner sleeve shown in FIG. 5, wherein the left part shows a cross-sectional view.
Figure 15:
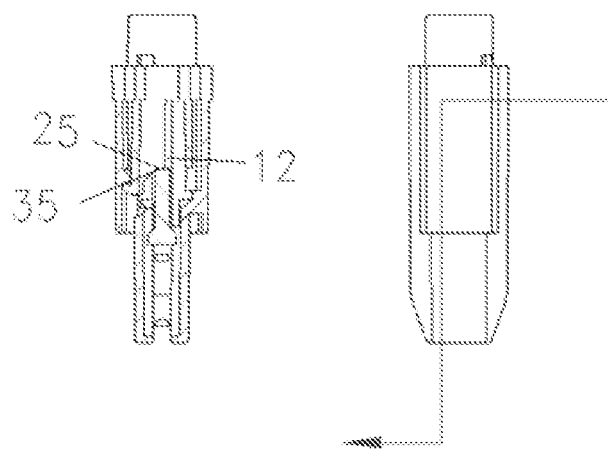
FIG. 15 is a schematic cross-sectional view of the lancet shown in FIG. 14, wherein the cross-sectional position is shown on the right side.

As shown in FIG. 7, a rear end 2b (lower end in the figure) of the inner sleeve 2 is provided with an abutment end face 25 perpendicular to the axial direction and adjacent to the second needle core guiding portion 24, and the needle core body 36 is adapted to abut against the abutment end face 25, as shown in FIG. 15. As it can be easily understood, the rotational movement of the inner sleeve 2 will cause the needle core body (more specifically contacting end face 35 thereof) to detach from the abutment end face 25 and move along the second needle core guiding portion 24 axially.

In the above-described lancet, as shown in FIG. 7, the rear end 2b (lower end in the figure) of the inner sleeve 2 is provided with a guide unit 21 which is cooperated with the inner sleeve guiding portion 13. A more specific embodiment of the guide unit 21 will be described later in detail.

In an alternative embodiment, the guide unit 21 is a guiding protrusion, and the above-mentioned guiding portions are guiding grooves. However, alternatively, the guide unit can also be a groove provided to the inner sleeve, while the guiding portion may be a guiding rib provided to the housing.

Alternatively, as shown in FIG. 4, the inner sleeve guiding portion 13 is provided inside with an inner sleeve positioning member 14. The inner sleeve positioning member 14 cooperates with the guide unit 21 to allow the guide unit 21 to pass over the inner sleeve positioning member 14 in a direction of moving towards the rotary guiding section 15 and to prevent the guide unit 21 from passing through the inner sleeve positioning member 14 in a direction of moving away from the rotary guiding section 15.

More specifically, as shown in FIG. 7, the guide unit 21 has a first guiding ramped surface 211 and a first vertical blocking surface 212, wherein when the guide unit 21 moves towards the rotary guiding section 15 (that is, when the inner sleeve 2 is pressed inwards the housing 1), the first guiding ramped surface 211 is adapted to contact with the inner sleeve positioning member 14, and after the guide unit 21 passes over the inner sleeve positioning member 14, the first vertical blocking surface 212 constitutes a blocking portion to prevent the guide unit 21 from passing over the inner sleeve positioning member 14.

More specifically, as shown in FIG. 4, the inner sleeve positioning member 14 has a second guiding ramped surface 141 and a second vertical blocking surface 142, wherein the second guiding ramped surface cooperates with the first guiding ramped surface, and the second vertical blocking surface cooperates with the first vertical blocking surface.

Figure 12:
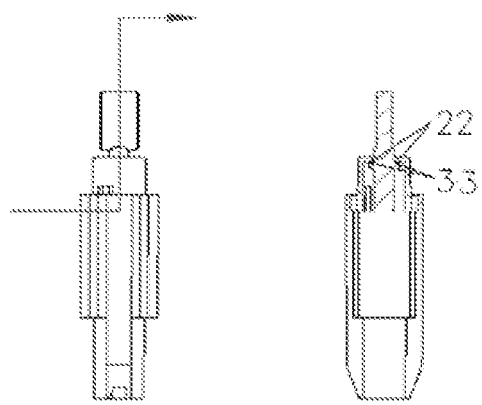
FIG. 12 is a schematic cross-sectional view of the lancet shown in FIG. 11, wherein the cross-sectional position is shown on the left side.

In the lancet above, as shown in FIG. 8, the needle core 3 further includes a needle cap 34 provided to the needle core body. The needle cap 34 passes through the inner sleeve through the inner sleeve needle outlet 26 and the needle cap 34 has a cap stopping member 33 which abuts against an inner end face 22 of the front end 2a of the inner sleeve 2 due to the potential energy of the spring 4, as shown in FIG. 12.

As shown in FIG. 6, the inner sleeve needle outlet 26 is provided with an open channel that allows the needle cap stopping member 33 to pass through only in a specific orientation: only when the needle cap stopping member 33 aligns with upper and lower small channels of the inner sleeve needle outlet 26 shown in FIG. 6, the needle cap stopping member 33 can be removed from the inner sleeve needle outlet 26, otherwise the needle cap stopping member 33 will abut against the inner surface of the front end 2a of the inner sleeve.

Figure 13:
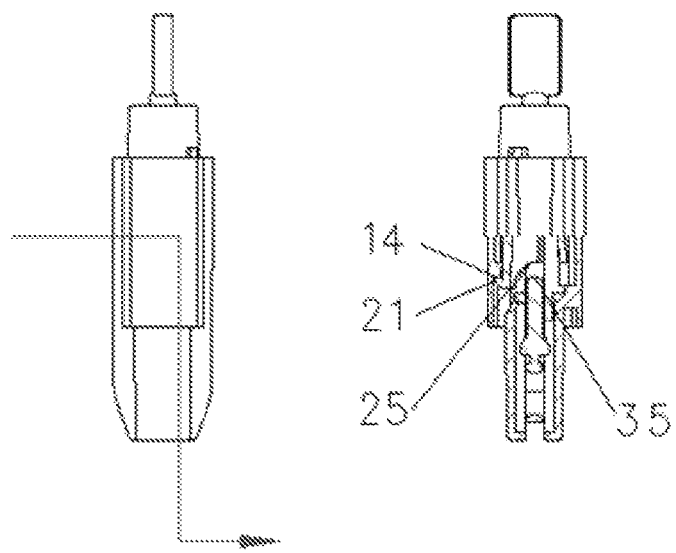
FIG. 13 is a schematic cross-sectional view of the lancet shown in FIG. 11, wherein the cross-sectional position is shown on the left side.

As shown in FIG. 13, when the guide unit 21 has passed over the inner sleeve positioning member 14 and thus abuts against the inner sleeve positioning member 14, the distance between the needle core body (that is, the contacting end face 35 thereof) and the abutted end face 25 is within the range of 1 mm-2 mm.

It should be noted that in the present disclosure, the inner sleeve positioning member 14 is not necessary. In the case where the inner sleeve positioning member is not provided, the guide member 21 needs not to be provided with structures for engaging therewith to, as long as it can engage with the inner sleeve guiding portion 13. A protrusion may be provided to the outer wall of the inner sleeve 2, and the protrusion cooperates with a stopper which is adjacent to the outlet of the housing 1 and provided to the housing 1.

It should be noted that the cooperation mode between the first needle core guiding portion and the guide on the needle (for example, the protrusion 31) is not limited to the manners mentioned in the embodiment of the present disclosure.

It should be pointed out that in the case where the rotary guiding section of the present disclosure is employed, the length of the inner sleeve 2 protruding out of the housing 1 before the operation should satisfy the requirement that the inner sleeve 2 can be rotated so that the first needle core guiding portion and the second needle core guiding section are aligned or centered in the radial direction. In a specific embodiment, by the rotary guiding section, the inner sleeve 2 is rotated by 25° to 35° (more specifically) 30° along the axis of the lancet, and simultaneously moves axially inwards by 2.5 mm to 3.5 mm (more specifically 3 mm).

It should be pointed out that the length of the abutment end face 25 of the inner sleeve 2 should also be adapted to the length of the inner sleeve 2 protruding out of the housing 1 before operation. In other words, before the inner sleeve 2 completely enters the housing 1, the abutting end surface 25 of the inner sleeve 2 should be moved beyond the abutting end surface 35 of the needle 3, or the circumferential distance that the abutting end surface 25 of the inner sleeve 2 contacts with the abutting end surface 35 of the needle 3 is smaller than the circumferential distance by which the inner sleeve rotates in the radial direction. In a specific embodiment, before operation, the distance between the abutting end surface 25 of the inner sleeve 2 and the limiting end face 16 is slightly 1-2 mm smaller than the length of the outer sleeve 2 extending out of the housing 1. It should be noted that it is also feasible that the needle core 3 is not provided with the protrusion 33. In that case, the abutting end surface 35 of the needle core 3 can directly abut against the abutting end surface 25 of the inner sleeve 2.

The assembly process of the lancet in the present disclosure will be described below with reference to the structures shown above.

First, the spring 4 is placed to a spring positioning post 11 of the housing 1. Second, two symmetrical protrusions 31 on both sides of the needle core 3 are installed along the two symmetrical needle core guiding grooves 12 inside the housing, and a spring catch point 32 at the tail of the needle core is then inserted into the spring 4. Third, the inner sleeve buckle or the guide unit 21 is aligned with and inserted into the inner sleeve guiding groove 13 of the housing and stops after passing over the inner sleeve positioning member 14 of the housing. The inner sleeve positioning member 14 of the housing 1 prevents the inner sleeve 2 from passing over it and thus moving axially towards outside the housing 1. In this case, the stopping members 33 symmetrical on both sides of the needle cap abut against the inner sleeve abutting end surface 22 with the spring potential energy.

In this way, even if the inner sleeve 2 retracts upon the pressing force on the front end face 23 of the inner sleeve 2, the potential energy of the spring 4 can still support the needle core and allow the inner sleeve 2 to get back when the pressing force on the inner sleeve 2 is withdrawn, which provides a protection mechanism to the lancet to avoid false emission when a special cap is not required.

The operation procedure of the lancet in the exemplary embodiment of the present disclosure will be described below with reference to the above-described structure.

Figure 11:
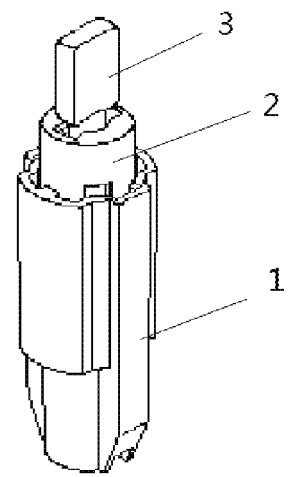
FIG. 11 is a schematic structural view of the lancet according to one exemplary embodiment of the present disclosure before use.

FIG. 11 is a schematic structural view of a lancet in the exemplary embodiment of the present disclosure before use. Prior to use, as shown in FIG. 12, the needle cap stopping members 33 of the needle 3 abut against the inner end surface 22 of the front end 2a of the inner sleeve 2 (pushing the inner sleeve towards the outside of the housing), and at the same time, as shown in FIG. 13, the guide unit 21 of the inner sleeve 2 engages with the inner sleeve positioning member 14 of the housing 1 (preventing the inner sleeve 2 from being pushed towards the outside of the housing 1). At this time, there is a safety distance between the contact end surface 35 of the needle core 3 and the abutting end surface 25 of the inner sleeve 2, for example, 1 mm-2 mm, which can effectively prevent the failure of the false emission prevention structure.

Figure 14:
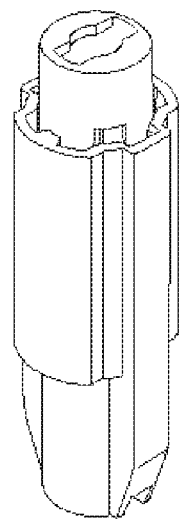
FIG. 14 is a schematic view of the lancet shown in FIG. 11 with the needle cap being removed.

When it is desired to remove the needle cap 34 to facilitate further use, first, the needle cap 34 is rotated, and then the needle cap 34 is removed via the inner sleeve needle outlet 26 to expose the needle tip of the needle core body 36 which is wrapped by the needle cap. The state of the lancet after removal of the needle cap 34 is shown in FIGS. 14-15.

After the removal of the needle cap 34, the inner sleeve 2 shown in FIG. 13 loses the support of the needle cap stopping members 33 on both sides of the needle cap, and correspondingly, the needle core 3 also loses support from the needle cap stopping members 33 on both sides of the needle cap. With the spring potential, the needle core 3 moves a certain distance along the needle guiding groove 12 axially towards the inner sleeve needle outlet 26 until the front end faces or contacting end surfaces 35 of the symmetrical protrusions 31 on both sides of the needle core abut against the inner sleeve abutting end surfaces 25, as shown in FIG. 15. At this time, the needle core 3 cannot move axially. Because the protrusions 31 on both sides of the needle core 3 are pre-installed in the guiding grooves 12 of the housing 1, the needle core 3 only moves along the guiding grooves 12 in the axial direction.

Figure 18:
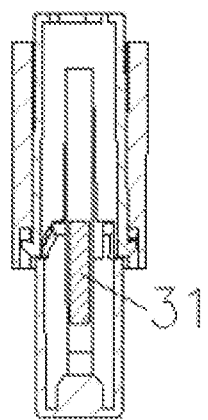
FIG. 18 schematically shows the position of the needle core when it is ready to be emitted.

In the blood taking operation, as shown in FIG. 17, a pressing force F is applied to the front end surface 23 of the inner sleeve to move the inner sleeve 2 axially along the inner sleeve guiding groove 13 of the outer housing 1 towards the inside of the housing 1, and the inner sleeve buckle or the guide unit 21 continues to slide along the inner sleeve guiding groove 13 of the housing 1 towards the inside of the housing. After passing through the rotary guiding section 15 of the housing, the inner sleeve buckle or the guide unit 21 not only moves in the axial direction but also rotates a certain angle radially along the rotary guiding section of the housing until the inner sleeve buckle or guide unit 21 contacts with the limiting end face 16 of the rotary guiding section 15 of the housing 1 and thus stops sliding. However, the symmetrical protrusions 31 on both sides of the needle core will be limited by the needle guiding grooves 12 of the housing 1 and thus will not rotate with the inner sleeve 2. In this case, the needle guiding groove 24 of the inner sleeve 2 is aligned with the needle guiding groove 12 of the housing (that is, they are aligned in the radial direction so that the protrusions 31 of the needle core can slide axially in the guiding grooves 24 and 12). FIG. 18 schematically shows the positions of the needle core or the protrusions 31 on both sides of the needle core in emission.

The contact end surfaces 35 of the symmetrical protrusions 31 on both sides of the needle core then disengage with the inner sleeve abutment end faces 25 so that the needle core 3 without being controlled or blocked by the inner sleeve abutment end faces 25 is in an unconstrained state in the axial direction, and the needle core 3 can be emitted and strike along the needle guiding grooves 12 of the housing 1 and the needle guiding grooves 24 of the inner sleeve by the spring potential energy. The needle tip of the inner steel needle of the needle core 3 passes through the inner sleeve needle outlet 26 to puncture the skin of the patient and is then retracted into the housing 1 upon the spring tension, and the blood collection is completed.

Figure 16:
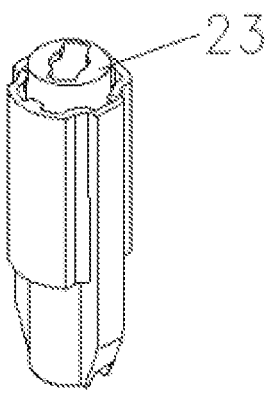
FIG. 16 is a schematic view of the lancet shown in FIG. 11 after use.

The state of the lancet after use is shown in FIG. 16. The used needle cannot be restored to its original position to avoid secondary use.

Although embodiments of the present disclosure have been explained and described, it will be understood that changes may be made to these embodiments by those skilled in the art without departing from the principles and spirit of the present disclosure. The scope of the present disclosure is defined by the appended claims and their equivalents.

The invention claimed is:

1. A lancet comprising:
an inner sleeve;
a needle core;
a housing extending along a longitudinal axis from a first side to a second side, the housing comprising an inner sleeve guiding portion extending along the longitudinal axis from the first side towards the second side and configured to guide movement of the inner sleeve, and a first needle core guiding portion configured to guide movement of the needle core;
the inner sleeve provided inside the housing and configured to move along the inner sleeve guiding portion, wherein the inner sleeve comprises an inner sleeve needle outlet provided on a front end of the inner sleeve, and a second needle core guiding portion;
the needle core comprising a needle core body configured to move axially along the first needle core guiding portion, and a needle body; and
a spring provided inside the housing to drive the needle core to move axially towards the inner sleeve needle outlet,
wherein:
the first needle core guiding portion is a first needle core guiding groove which extends axially along the housing;
the second needle core guiding portion extends axially and is a second needle core guiding groove;
the housing further comprises a rotation guiding groove which has a radial rotation angle and is disposed at a position closer to the second side of the housing than the inner sleeve guiding portion, and which is configured to guide a guiding protrusion at a rear end of the inner sleeve so as to guide the inner sleeve to rotate with the radial rotation angle at the rotation guiding groove;
the inner sleeve, when pressed from the front end of the inner sleeve towards the inside of the housing, is configured to be guided by the rotation guiding groove to rotate such that the first needle core guiding portion is aligned with the second needle core guiding portion in a radial direction;
the rotation guiding groove comprises a limiting end face perpendicular to an axial direction;
the guiding protrusion is configured to cooperate with the inner sleeve guiding portion and with the rotation guiding groove, and the inner sleeve guiding portion is a guiding groove; and
the housing comprises an inner sleeve positioning surface, provided between the inner sleeve guiding portion and the rotation guiding groove, the guiding protrusion is provided with a first guiding ramped surface and a first vertical blocking surface, wherein when the guiding protrusion moves towards the rotation guiding groove, the first guiding ramped surface is configured to contact the inner sleeve positioning surface to allow the guiding protrusion to pass over the inner sleeve positioning surface, and after the guiding protrusion passes over the inner sleeve positioning surface, the first vertical blocking surface is configured to prevent the guiding protrusion from passing back over the inner sleeve positioning surface.

2. The lancet according to claim 1, wherein the radial rotation angle of the rotation guiding groove is between 25° and 35°.

3. The lancet according to claim 1, wherein:
the inner sleeve further comprises an abutment end face perpendicular to the axial direction at the rear end of the inner sleeve adjacent to the second needle core guiding portion;
the needle core body is configured to abut against the abutment end face; and
a rotational movement of the inner sleeve causes the needle core body to be out of contact with the abutment end face and to move axially along the second needle core guiding portion.

4. The lancet according to claim 1, wherein:
the inner sleeve positioning surface comprises a member, wherein the member is provided with a second guiding ramped surface and a second vertical blocking surface; and
when the guiding protrusion is configured to move towards the rotation guiding groove, the second guiding ramped surface cooperates with the first guiding ramped surface to allow the guiding protrusion to pass over the inner sleeve positioning surface, and after the guiding protrusion passes over the inner sleeve positioning surface, the second vertical blocking surface cooperates with the first vertical blocking surface to prevent the guiding protrusion from passing back over the inner sleeve positioning surface.

5. The lancet according to claim 1, wherein:
the needle core further comprises a needle cap provided to the needle core body, wherein the needle cap is configured to pass through the inner sleeve through the inner sleeve needle outlet, the needle cap comprises a needle cap stopping protrusion which extends radially outwards from an outer wall of the needle cap, and the needle cap stopping protrusion is configured to abut against an inner end face of the inner sleeve with a potential energy of the spring;
the inner sleeve needle outlet is provided with an opening channel that allows the needle cap stopping protrusion to pass through only in a specific orientation;
the inner sleeve further comprises an abutment end face perpendicular to the axial direction at the rear end of the inner sleeve adjacent to the second needle core guiding portion;
the needle core body is configured to abut against the abutment end face; and
when the guiding protrusion passes over the inner sleeve positioning surface and abuts against the inner sleeve positioning surface, the distance between the needle core body and the abutment end face is in the range of 1 mm to 2 mm.

6. The lancet according to claim 4, wherein:
the needle core further comprises a needle cap provided to the needle core body, wherein the needle cap is configured to pass through the inner sleeve through the inner sleeve needle outlet, the needle cap comprises a needle cap stopping protrusion which extends radially outwards from an outer wall of the needle cap, and the needle cap stopping protrusion is configured to abut against an inner end face of the inner sleeve with a potential energy of the spring;
the inner sleeve needle outlet is provided with an opening channel that allows the needle cap stopping protrusion to pass through only in a specific orientation;
the inner sleeve further comprises an abutment end face perpendicular to the axial direction at the rear end of the inner sleeve adjacent to the second needle core guiding portion;
the needle core body is configured to abut against the abutment end face; and
when the guiding protrusion passes over the inner sleeve positioning surface and abuts against the inner sleeve positioning surface, the distance between the needle core body and the abutment end face is in the range of 1 mm to 2 mm.

7. A lancet comprising:
an inner sleeve;
a needle core;
a housing extending along a longitudinal axis from a first side to a second side, the housing comprising an inner sleeve guiding portion extending along the longitudinal axis from the first side towards the second side and configured to guide movement of the inner sleeve, and a first needle core guiding portion configured to guide movement of the needle core;
the inner sleeve provided inside the housing and configured to move along the inner sleeve guiding portion, wherein the inner sleeve comprises an inner sleeve needle outlet provided on a front end of the inner sleeve, and a second needle core guiding portion;
the needle core comprising a needle core body configured to move axially along the first needle core guiding portion, and a needle body; and
a spring provided inside the housing to drive the needle core to move axially towards the inner sleeve needle outlet,
wherein:
the first needle core guiding portion is a first needle core guiding groove which extends axially along the housing;
the second needle core guiding portion extends axially and is a second needle core guiding groove;
the housing further comprises a rotation guiding groove which has a radial rotation angle and is disposed at a position closer to the second side of the housing than the inner sleeve guiding portion, and which is configured to guide a guiding protrusion at a rear end of the inner sleeve so as to guide the inner sleeve to rotate with the radial rotation angle at the rotation guiding groove;
the inner sleeve, when pressed from the front end of the inner sleeve towards the inside of the housing, is configured to be guided by the rotation guiding groove to rotate such that the first needle core guiding portion is aligned with the second needle core guiding portion in a radial direction;
the rotation guiding groove comprises a limiting end face perpendicular to an axial direction;
the guiding protrusion is configured to cooperate with the inner sleeve guiding portion and with the rotation guiding groove, and the inner sleeve guiding portion is a guiding groove; and the radial rotation angle of the rotation guiding groove is between 25° and 35° and the inner sleeve is configured to be axially displaced by 2.5 mm-3.5 mm based on the guidance of the entire rotation guiding groove.

8. A lancet comprising:
an inner sleeve;
a needle core;
a housing extending along a longitudinal axis from a first side to a second side, the housing comprising an inner sleeve guiding portion extending along the longitudinal axis from the first side towards the second side and configured to guide movement of the inner sleeve, and a first needle core guiding portion configured to guide movement of the needle core;
the inner sleeve provided inside the housing and configured to move along the inner sleeve guiding portion, wherein the inner sleeve comprises an inner sleeve needle outlet provided on a front end of the inner sleeve, and a second needle core guiding portion;
the needle core comprising a needle core body configured to move axially along the first needle core guiding portion, and a needle body; and a spring provided inside the housing to drive the needle core to move axially towards the inner sleeve needle outlet,
wherein:
the first needle core guiding portion is a first needle core guiding groove which extends axially along the housing;
the second needle core guiding portion extends axially and is a second needle core guiding groove;
the housing further comprises a rotation guiding groove which has a radial rotation angle and is disposed at a position closer to the second side of the housing than the inner sleeve guiding portion, and which is configured to guide a guiding protrusion at a rear end of the inner sleeve so as to guide the inner sleeve to rotate with the radial rotation angle at the rotation guiding groove;

the inner sleeve, when pressed from the front end of the inner sleeve towards the inside of the housing, is configured to be guided by the rotation guiding groove to rotate such that the first needle core guiding portion is aligned with the second needle core guiding portion in a radial direction;

the inner sleeve further comprises an abutment end face perpendicular to an axial direction at the rear end of the inner sleeve adjacent to the second needle core guiding portion;

the needle core body is configured to abut against the abutment end face;

a rotational movement of the inner sleeve causes the needle core body to be out of contact with the abutment end face and to move axially along the second needle core guiding portion;

the guiding protrusion is configured to cooperate with the inner sleeve guiding portion and with the rotation guiding groove, and the inner sleeve guiding portion is a guiding groove; and the housing comprises an inner sleeve positioning surface, provided between the inner sleeve guiding portion and the rotation guiding groove, the guiding protrusion is provided with a first guiding ramped surface and a first vertical blocking surface, wherein when the guiding protrusion moves towards the rotation guiding groove, the first guiding ramped surface is configured to contact the inner sleeve positioning surface to allow the guiding protrusion to pass over the inner sleeve positioning surface, and after the guiding protrusion passes over the inner sleeve positioning surface, the first vertical blocking surface is configured to prevent the guiding protrusion from passing back over the inner sleeve positioning surface.

9. The lancet according to claim 8, wherein the rotation guiding groove comprises a limiting end face perpendicular to the axial direction.

10. The lancet according to claim 8, wherein the radial rotation angle of the rotation guiding groove is between 25° and 35°.

11. A lancet comprising:
an inner sleeve;
a needle core;
a housing extending along a longitudinal axis from a first side to a second side, the housing comprising an inner sleeve guiding portion extending along the longitudinal axis from the first side towards the second side and configured to guide movement of the inner sleeve, and a first needle core guiding portion configured to guide movement of the needle core;

the inner sleeve provided inside the housing and configured to move along the inner sleeve guiding portion, wherein the inner sleeve comprises an inner sleeve needle outlet provided on a front end of the inner sleeve, and a second needle core guiding portion to guide the movement of the needle core;

the needle core comprising which comprises a needle core body configured to move axially along the first needle core guiding portion, and a needle body; and a spring provided inside the housing to drive the needle core to move axially towards the inner sleeve needle outlet, wherein:
the first needle core guiding portion is a first needle core guiding groove which extends axially along the housing;

the second needle core guiding portion extends axially and is a second needle core guiding groove;

the housing further comprises a rotation guiding groove which has a radial rotation angle and is disposed at a position closer to the second side of the housing than the inner sleeve guiding portion, and which is configured to a guiding protrusion at a rear end of guide the inner sleeve so as to guide the inner sleeve to rotate with a radial rotation angle at the rotation guiding groove;

the inner sleeve, when pressed from the front end of the inner sleeve towards the inside of the housing, is configured to be guided by the rotation guiding groove to rotate such that the first needle core guiding portion is aligned with the second needle core guiding portion in a radial direction;

the guiding protrusion is configured to cooperate with the inner sleeve guiding portion and with the rotation guiding groove, and the inner sleeve guiding portion is a guiding groove;

the inner sleeve further comprises an abutment end face perpendicular to an axial direction at a rear end of the inner sleeve adjacent to the second needle core guiding portion;

the needle core body is configured to abut against the abutment end face;

a rotational movement of the inner sleeve causes the needle core body to be out of contact with the abutment end face and to move axially along the second needle core guiding portion;

the rotation guiding groove comprises a limiting end face perpendicular to an axial direction; and the inner sleeve is configured to be axially displaced by 2.5 mm-3.5 mm based on the guidance of the entire rotation guiding groove.

* * * * *